(12) United States Patent
Kim et al.

(10) Patent No.: US 7,294,269 B2
(45) Date of Patent: Nov. 13, 2007

(54) ORGANIC DISPOSER AND METHOD OF CONTROLLING THE SAME

(75) Inventors: Yong Gu Kim, Seoul (KR); Tae Hee Kwak, Incheon (KR)

(73) Assignee: LG Electronics Inc., Seoul (KR)

( * ) Notice: Subject to any disclaimer, the term of this patent is extended or adjusted under 35 U.S.C. 154(b) by 399 days.

(21) Appl. No.: 11/095,560

(22) Filed: Apr. 1, 2005

(65) Prior Publication Data

US 2006/0076292 A1  Apr. 13, 2006

(30) Foreign Application Priority Data

Oct. 7, 2004  (KR) .................. 10-2004-0079996

(51) Int. Cl.
*C02F 3/00* (2006.01)

(52) U.S. Cl. .................. 210/609; 210/612; 210/784; 210/138; 210/149; 210/175

(58) Field of Classification Search ............... 210/609, 210/612, 784, 138, 149, 175
See application file for complete search history.

(56) References Cited

FOREIGN PATENT DOCUMENTS

| KR | 1998-63279 | 11/1998 |
|---|---|---|
| KR | 2000-11976 | 7/2000 |

OTHER PUBLICATIONS

English Lnaguage Abstract of Korean 1998-63279.
English Language Abstract of Korean 2000-11976.

*Primary Examiner*—Chester T Barry
(74) *Attorney, Agent, or Firm*—Greenblum & Bernstein, P.L.C.

(57) ABSTRACT

An organic matter disposer is disclosed, including a tub, a drum rotatably provided in the tub so as to store organic matters therein, a stirrer provided in the drum so as to stir the organic matters, a driving device for rotating the drum and the stirrer, and a heating device for drying the organic matters.

26 Claims, 6 Drawing Sheets

ORGANIC DISPOSER AND METHOD OF CONTROLLING THE SAME

CROSS-REFERENCE TO RELATED APPLICATIONS

This application claims the benefit of Korean Application No. P2004-79996, filed on Oct. 7, 2004.

BACKGROUND OF THE INVENTION

1. Field of the Invention

The present invention relates to an organic matter disposer, and more particularly, to an organic matter disposer and a controlling method thereof.

2. Discussion of the Related Art

In general, an organic matter disposer is divided into a hot-air drying system and a fermenting system. The hot-air drying system blows hot temperature air to organic matters so as to dry the organic matters by evaporating moisture contained in the organic matters. The fermenting system is maintained at a proper temperature for making a proper condition for fermentation so as to ferment the organic matters by using fermentative microbes.

A conventional organic matter disposer has problems as follows. First, since the hot-air system dries the organic matters by blowing hot temperature air to the organic matters, electric power consumed by a heater for heating air is largely increased. Particularly, the problem is remarkable when organic matters containing a large amount of water are dried. Second, since the fermenting system ferments the organic matters at a relatively lower temperature, electric power consumption is lowered, but on the other hand, a fermenting time is longer than the hot-air heating system. Third, in the hot-air system or the fermenting system, degree of dryness or ferment is changed according to an amount of moisture contained in the organic matters.

SUMMARY OF THE INVENTION

Accordingly, the present invention is directed to an organic matter disposer and a controlling method thereof that substantially obviates one or more problems due to limitations and disadvantages of the related art.

An object of the present invention is to provide an organic matter disposer and a controlling method thereof enabling to shorten a time of discarding organic matters and to reduce electric consumption.

Another object of the present invention is to provide an organic matter disposer and a controlling method thereof enabling to equalize degrees of dryness and fermentation of organic matters.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an organic matter disposer includes a tub, a drum rotatably provided in the tub so as to store organic matters therein, a stirrer provided in the drum so as to stir the organic matters, a driving device for rotating the drum and the stirrer, and a heating device for drying the organic matters.

The drum includes a body having at least one through holes so as to discharge moisture contained in the organic matters. The drum further includes a screen having a mesh for passing moisture through the through holes and filtering organic matters. The screen is attached to an inner or outer surface of the body.

The organic matter disposer further includes a fermentative microbe supplying unit provided at an upper part of the drum so as to supply fermentative microbes to the organic matters.

The driving device includes a dehydrating axis coupled with the drum, a stirrer axis rotatably provided in the dehydrating axis and coupled with the stirrer, a clutching device provided to selectively connect the dehydrating axis with the stirrer, and a motor for rotating the stirrer axis.

The stirrer axis includes an upper stirrer axis connected with the stirrer, and a lower stirrer axis connected with the motor.

The organic matter disposer further includes a speed reducer provided between the upper stirrer axis and the lower stirrer axis so as to reduce rotational speed transmitted from the motor.

The speed reducer includes a sun gear provided at an upper end of the lower stirrer axis, a planetary gear connected with the sub gear, a first inner gear formed at a lower part of the upper stirrer axis so as to be selectively connected with the sun gear, and a second inner gear formed at a lower part of the first inner gear so as to be selectively connected with the sun gear.

The clutching device includes a coupling provided to be movable up and down at an outer circumference of the lower stirrer axis so as to be selectively connected with the dehydrating axis, and a clutch for moving the coupling up and down.

The heating device includes a heater for heating air, and a fan for blowing air into the tub, the air heated by the heater.

Meanwhile, a method of controlling an organic matter disposer includes a dehydrating step of discharging moisture contained in organic matters by rotating a drum and a stirrer at a predetermined speed, and a drying step of rotating the stirrer and blowing air into the drum, the air heated by the heating device.

In the drying step, the stirrer is rotated at a reduced speed.

In the dehydrating step, the drum and the stirrer are rotated at a same speed.

The method further includes, before the drying step, a preheating step of preheating the heating device.

The preheating step is performed for a predetermined time preset in a controlling member and then automatically stopped.

The dehydrating step is performed for a predetermined time preset in a controlling member and then automatically stopped.

The drying step is performed for a predetermined time preset in a controlling member and then automatically stopped.

Meanwhile, a method of controlling an organic matter disposer includes a dehydrating step of discharging moisture contained in organic matters by rotating a drum and a stirrer at a predetermined speed, a supplying step of supplying fermentative microbes into the drum, and a fermenting step of fermenting the organic matters by rotating the stirrer and blowing air into the drum, the air heated by a heating device.

The heating device keeps the inside of the drum at a proper temperature for fermentation.

In the fermenting step, the stirrer is rotated at a reduced speed.

In the dehydrating step, the drum and the stirrer are rotated at a same speed.

The method further includes, before the drying step, a preheating step of preheating the heating device.

The preheating step is performed for a predetermined time preset in a controlling member and then automatically stopped.

The dehydrating step is performed for a predetermined time preset in a controlling member and then automatically stopped.

The drying step is performed for a predetermined time preset in a controlling member and then automatically stopped.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
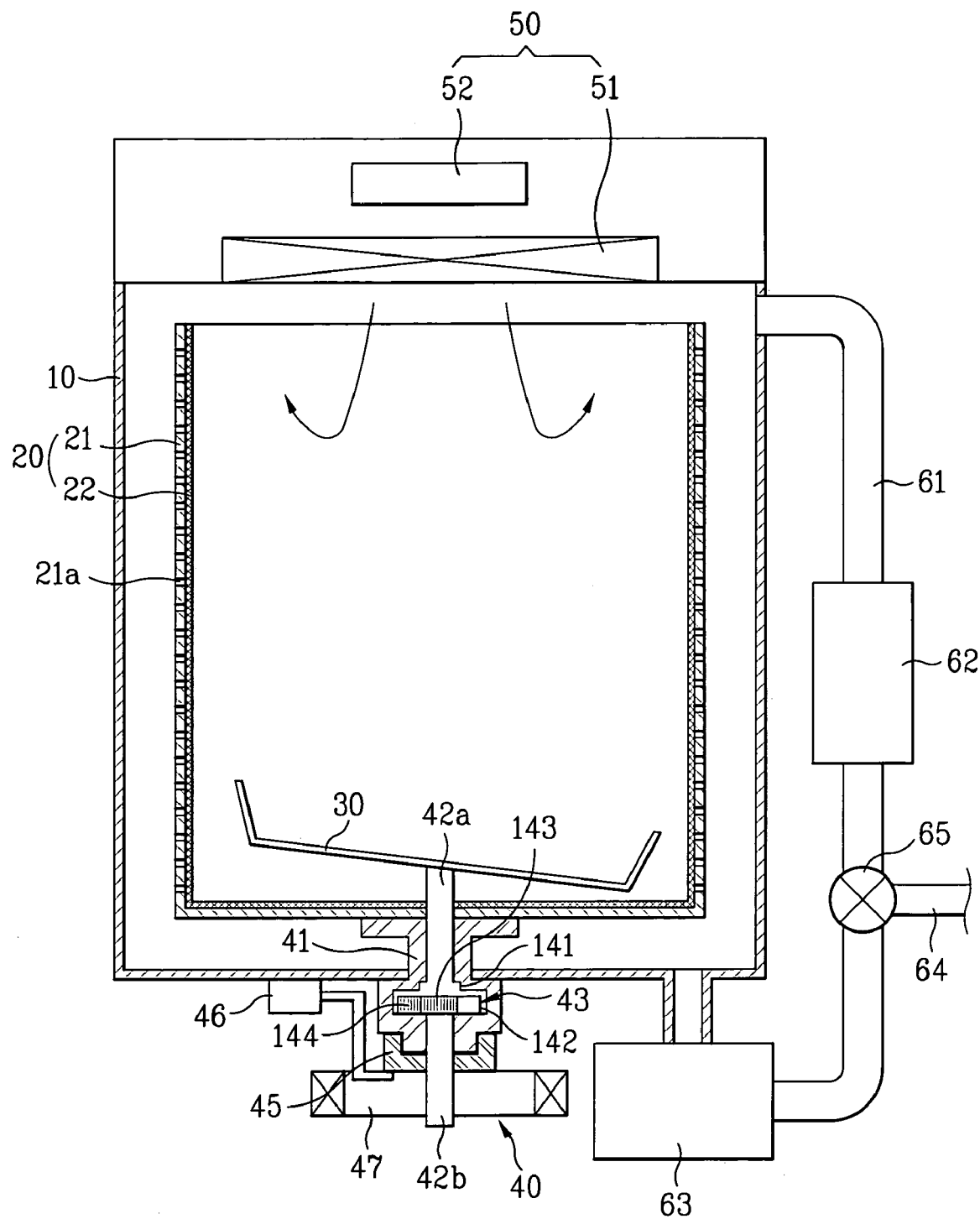
FIG. 1 illustrates a cross sectional view showing an organic matter disposer in accordance with a first embodiment of the present invention.

Hereinafter, an organic matter disposer in accordance with each embodiment of the present invention will be described referring to FIG. 1 to FIG. 6. FIG. 1 illustrates a structure of the organic matter disposer in accordance with the first embodiment of the present invention.

As shown in FIG. 1, the organic matter disposer includes a tub 10, a drum 20, a stirrer 30, a driving device 40, and a heating device 50. In this case, the tub 10 includes an exterior of the organic matter disposer, and the drum 20 for accommodating organic matters which are to be discarded is rotatably provided in the tub 10.

The driving device 40 is provided at a lower part of the tub 10, a stirrer 30 connected with the driving device 40 is rotatably provided in the drum, and the heating device 50 is provided at an upper part of the tub 10. In this case, according to the rotation of the drum 20, moisture contained in the organic matters is discharged to an outside of the drum. The organic matters include food contaminants.

The drum 20 includes a body 21 formed in a cylindrical form and having a plurality of through holes 21a, and a screen 22 having a mesh for filtering organic matters contained in water that passes through the plurality of through holes 21a on an inner circumference of the drum. In this case, the organic matters are mixed and dried according to the rotation of the drum. In this case, the body 21 and the screen 22 are made of a material such as synthetic resins, plastic, or stainless steel so as to supplement strength of the body 21 and the screen 22. Accordingly, the body 21 and the screen 22 resist gas generated from the organic matters or heat generated from the heating device 50 so as to remain in their original shapes.

Meanwhile, the screen 22 is attached to an outer surface or an inner surface of the body 21. The screen 22 passes moisture through the through holes, but filters the organic matters so as to prevent the organic matters from being discharged to an outside of the body. In this case, each piece of the screen may be attached to each of the plurality of through holes 21a on the body 21.

More or larger through holes 21a may be formed at a height of the drum 20, where moisture is best drained by the centrifugal force. The body 21 may of course include a porous material so as to function as a screen.

Meanwhile, the driving device 40 includes a dehydrating axis 41, a stirrer axis 42a and 42b, a speed reducer 43, a clutching device, and a motor. In this case, the dehydrating axis 41 is coupled with a lower part of the drum 20, and selectively coupled or decoupled with the stirrer axes 42a and 42b via the clutching device. The stirrer axes 42a and 42b are coupled with the stirrer 30 and the motor 47. In this instance, the motor 47 may include an inner rotor type having a rotor at a center thereof, or an outer rotor type having a rotor on an outside thereof. The speed reducer 43 is provided in the dehydrating axis so as to reduce rotational speed of the stirrer axis. The stirrer axis includes an upper stirrer axis 42a and a lower stirrer axis 42b, and a speed reducer 43 is provided between the upper and lower stirrer axes 42a and 42b.

The clutching device includes a coupling 45 provided to movable up and down on an outer circumference of the lower stirrer 42b, and a clutch 46 for moving the coupling up and down. In this case, the coupling 45 is desirably formed in a serration type and selectively coupled with a lower end of the dehydrating axis 41.

Since an upper end of the coupling 45 is coupled with the dehydrating axis 41 when the coupling 45 is moved upward, the stirrer axis and the dehydrating axis are rotated together. In other words, the dehydrating axis 41 and the stirrer axes 42a and 42b are rotated at a high speed when the coupling 45 is geared to the dehydrating axis 41.

On the other hand, since the upper end of the coupling 45 is separated from the dehydrating axis 41 when the coupling 45 is moved downward, only the stirrer axis is rotated. In other words, when the coupling 45 is released from the dehydrating axis 41, the dehydrating axis 41 remains still, but the stirrer axes 42a and 42b are rotated at a reduced speed.

Meanwhile, the rotational speed of the stirrer axes 42a and 42b are reduced by the speed reducer. In this case, the speed reducer 43 includes a sun gear 143 provided at an upper end of the lower stirrer axis 42b, and a planetary gear selectively geared with the sun gear 143. The upper stirrer axis 42a includes a first inner gear 141 formed at an inner lower end of the upper stirrer axis 42a and selectively geared with the sun gear 143, and a second inner gear 142 formed at a lower part thereof and geared with the planetary gear 144. When the sun gear 143 is geared with the planetary gear 144, the rotational speed of the stirrer axis 42a is reduced according to a gear ratio of the sun gear 143 and the planetary gear 144.

In this case, since the sun gear 143 is geared with the first inner gear 141 when the coupling 45 is moved upward, the upper stirrer axis 42a is rotated at a high speed. Meanwhile, the rotational speed of the stirrer axis 42a is reduced according to a gear ratio because the sun gear 143 is geared with the second inner gear 142 when the coupling 45 is moved downward.

Meanwhile, when the stirrer 30 is rotated, torque is increased because the stirrer 30 is rotated at a reduced speed. On the other hand, when the drum 20 is rotated together with the stirrer 30, the torque is reduced because the drum 20 is rotated at a relatively high speed. Besides the structure mentioned above, various types of the driving devices can be used for rotating the drum 20 and the stirrer 30 separately.

Meanwhile, the heating device 50 includes a heater 51, and a fan 52. Heat is generated by the heater 51 when electric power is supplied, and air heated by the heater 51 is blown into the tub 10 by the fan 52. In this case, the heater 51 needs to have enough calorific power so as to heat air and thereby to dry organic matters.

As shown in FIG. 1, a circulating duct 61 is provided at the tub 10 so as keep circulating the heated air. In other words, energy is saved by circulating the heated air in the tub through the circulating duct 61 instead of discharging to an outside thereof.

Both ends of the circulating duct 61 are communicated with inside of the tub 10. In this case, a deodorizing unit 62 and a water tank 63 are provided on a channel formed in the duct. In this case, water separated from organic matters is stored in the water tank 63. A discharging pipe 64 is coupled with a side of the duct 61 so as to selectively discharge a part of air to an outside thereof, and is selectively opened and closed by an opening and closing valve 65.

The organic matter disposer performs a dehydrating step and a drying step. Hereinafter, operations of the organic matter disposer in accordance with the first embodiment will be described referring to appended drawings.

Figure 2:
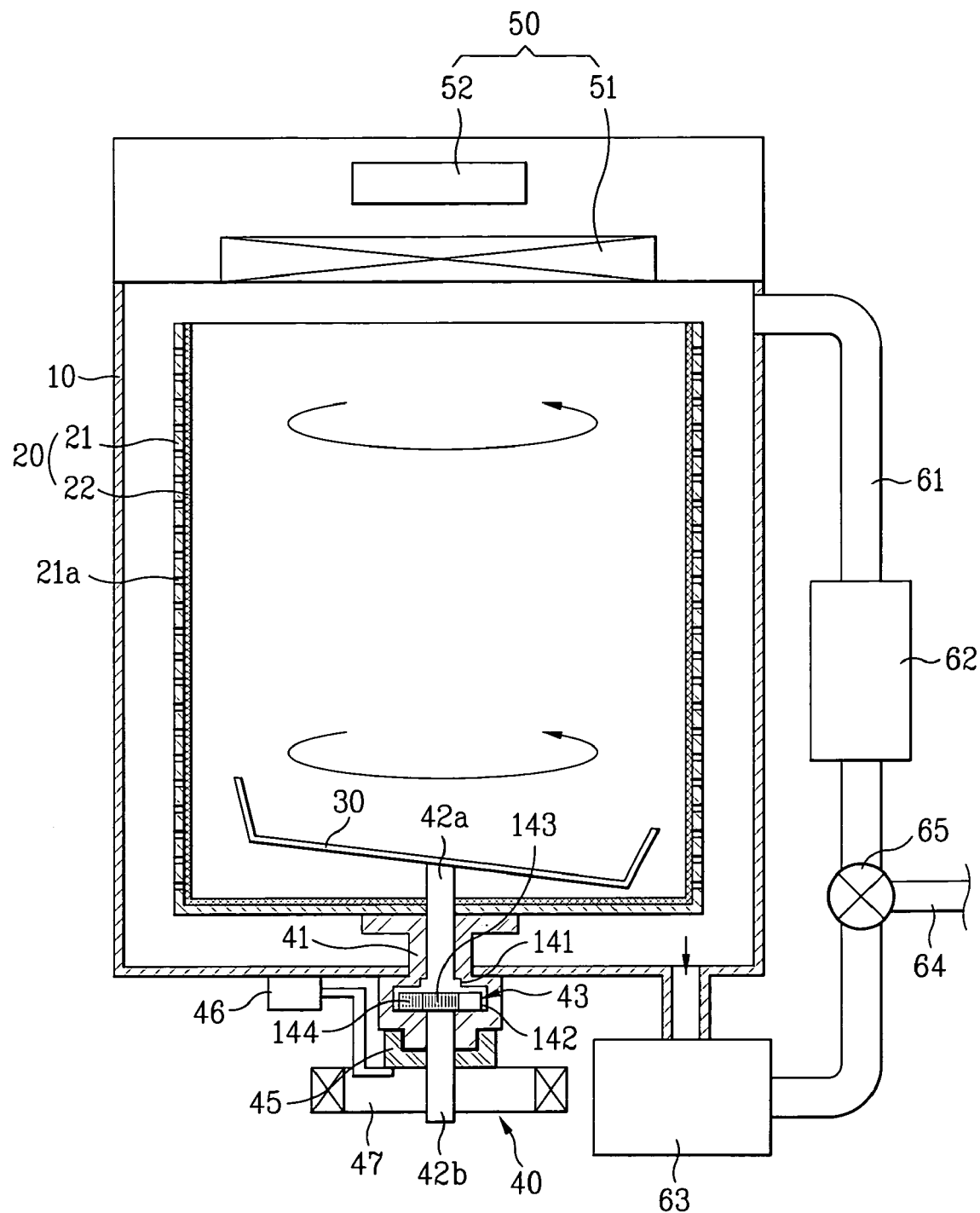
FIG. 2 illustrates a diagram showing an operating state of an organic matter disposer in accordance with the present invention.

Referring to FIG. 2, the dehydrating step will be described as follows. When organic matters are introduced into the drum 20 and electric power is supplied thereto, the motor is rotated. In this instance, the clutch 46 moved the coupling 45 upward such that coupling 45 is geared with the dehydrating axis 41. Accordingly, the stirrer axes 42a and 42b are rotated at a same speed.

Due to centrifugal force generated when the drum is rotated, moisture contained in the organic matters is discharged through the plurality of through holes 21a to the tub 10. In this instance, the screen 22 passes moisture therethrough, but filters organic matters at the same time so as to prevent the organic matters from being discharged. Moisture discharged to the tub 10 is collected in the water tank 63. When the dehydrating step is completed after a predetermined time, the drum 20 is stopped. Thereafter, the drying step is performed.

Figure 3:
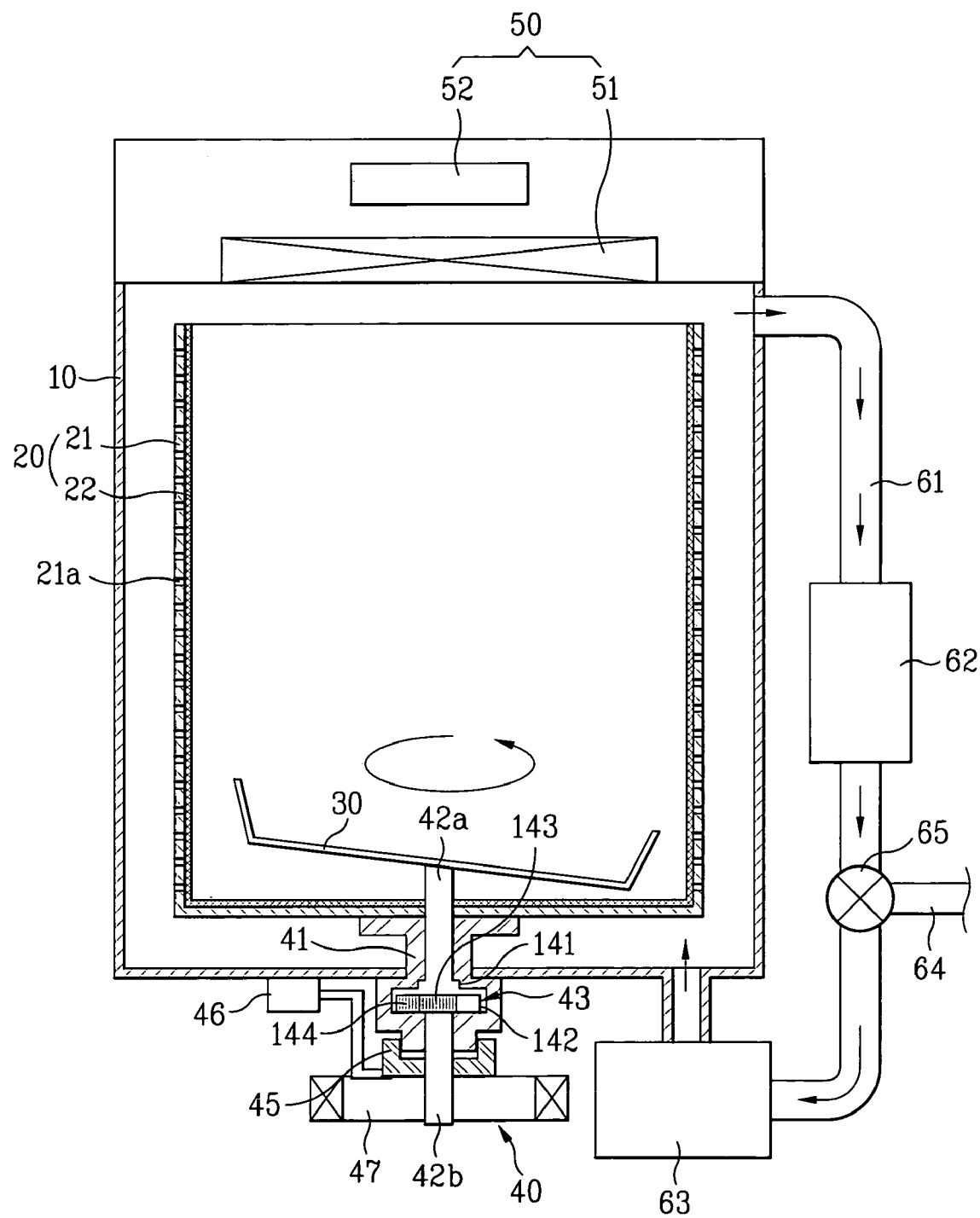
FIG. 3 illustrates a diagram showing an organic matter disposer when organic matters are dried.

Referring to FIG. 3, the drying step will be described as follows. When the drying step is started, the clutch 46 moves the coupling 45 downward so as to release the coupling geared with the dehydrating axis 41. Accordingly, only the stirrer axes 42a and 42b are rotated at a reduced speed. Therefore, only the stirrer 30 is rotated to stir the organic matters stored in the drum 20. In this case, the rotational speed of the stirrer 30 is reduced compared to that during the dehydrating step.

After the power supply to the heater 51, air is heated, and the heated air is flowed into the drum 20 along with the rotation of the fan 52. Accordingly, the organic matters are stirred by the stirrer 30 and heated so as to be dried.

As the organic matters are dried, gas is generated. The gas is circulated through the circulating duct 61. In this instance, the gas in the circulating duct 61 is deodorized by a deodorizer 62. When the drying step is completed, the opening and closing valve 65 is opened and a part of air is discharged to an outside thereof through the discharging pipe 64.

Figure 4:
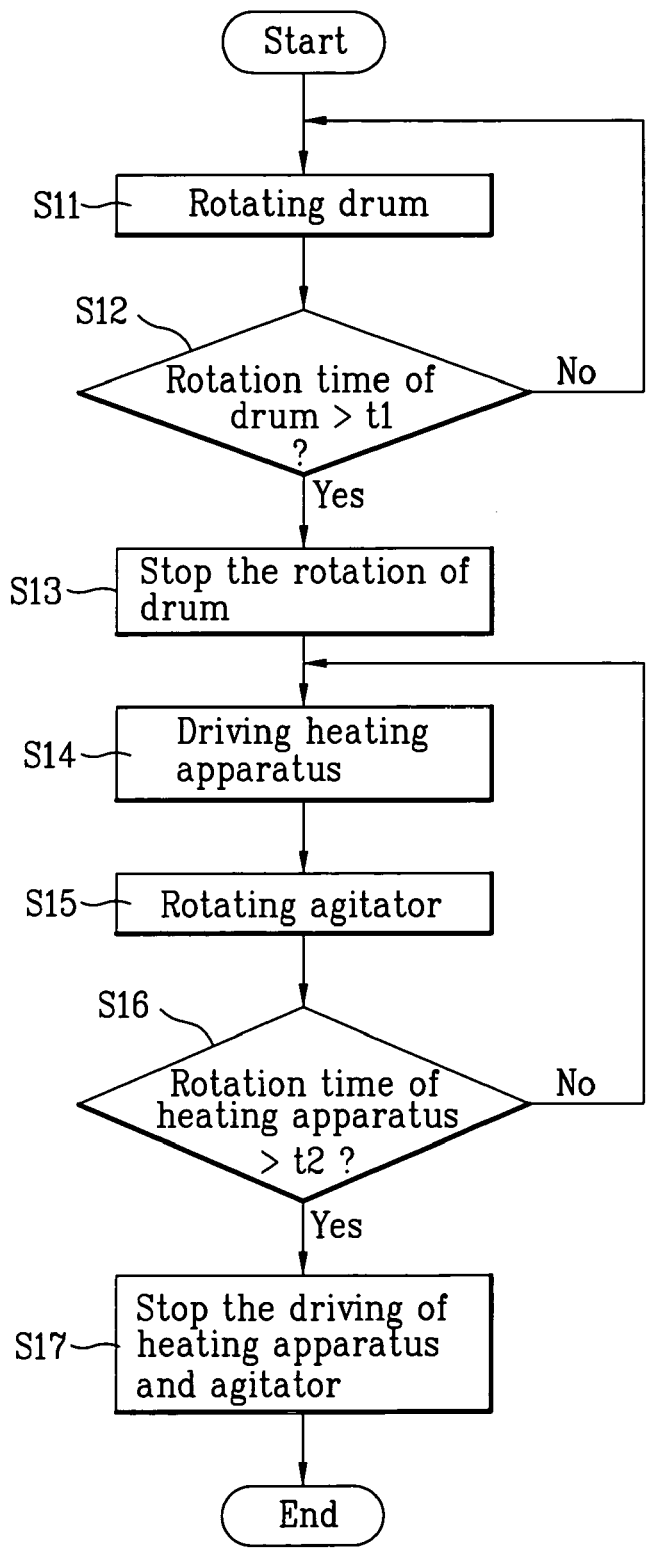
FIG. 4 illustrates a method of controlling an organic matter disposer in accordance with the first embodiment of the present invention.

FIG. 4 illustrates a flow chart showing a controlling method in accordance with the first embodiment of the present invention. AS shown in FIG. 4, when the dehydrating step is started, the drum is rotated (S11). In this instance, the drum is rotated so as to separate moisture contained in the organic matters. For example, the drum is rotated at a speed of 20-50 rpm.

After a predetermined time (t1) set in a controlling member is passed, the drum is stopped (S12 and S13). In this case, the set time (t1) is desirably set according to amount of the organic matters stored in the drum. A rotation time of the drum is set uniformly.

When the dehydrating step is completed, the drying step is started. The drying step can be started right after the dehydrating step is completed or after a predetermined time is passed.

When the heating device is operated for drying the organic matters, air heated by the heater is discharged to organic matters in the drum (S14). In this instance, a preheating step is desirably started a predetermined time before the drum is stopped because it takes some time for the heater to raise air temperature to a steady state temperature. In this case, in order to rapidly raise the temperature of the heater to a normal temperature, the fan is desirably stopped when the heater is preheated.

Organic matters are stirred by rotating the stirrer at a low speed (S15). Accordingly, a dehydrating time is decreased by increasing a contact area between organic matters and heated air, and the organic matters are uniformly dried.

When the driving time of the heating device is reached to a predetermined time (t2), the heating device and the stirrer are stopped (S16 and S17). In this case, the operating time of the heating device and the stirrer is desirably set in the controlling member according to an amount of organic matters.

Figure 5:
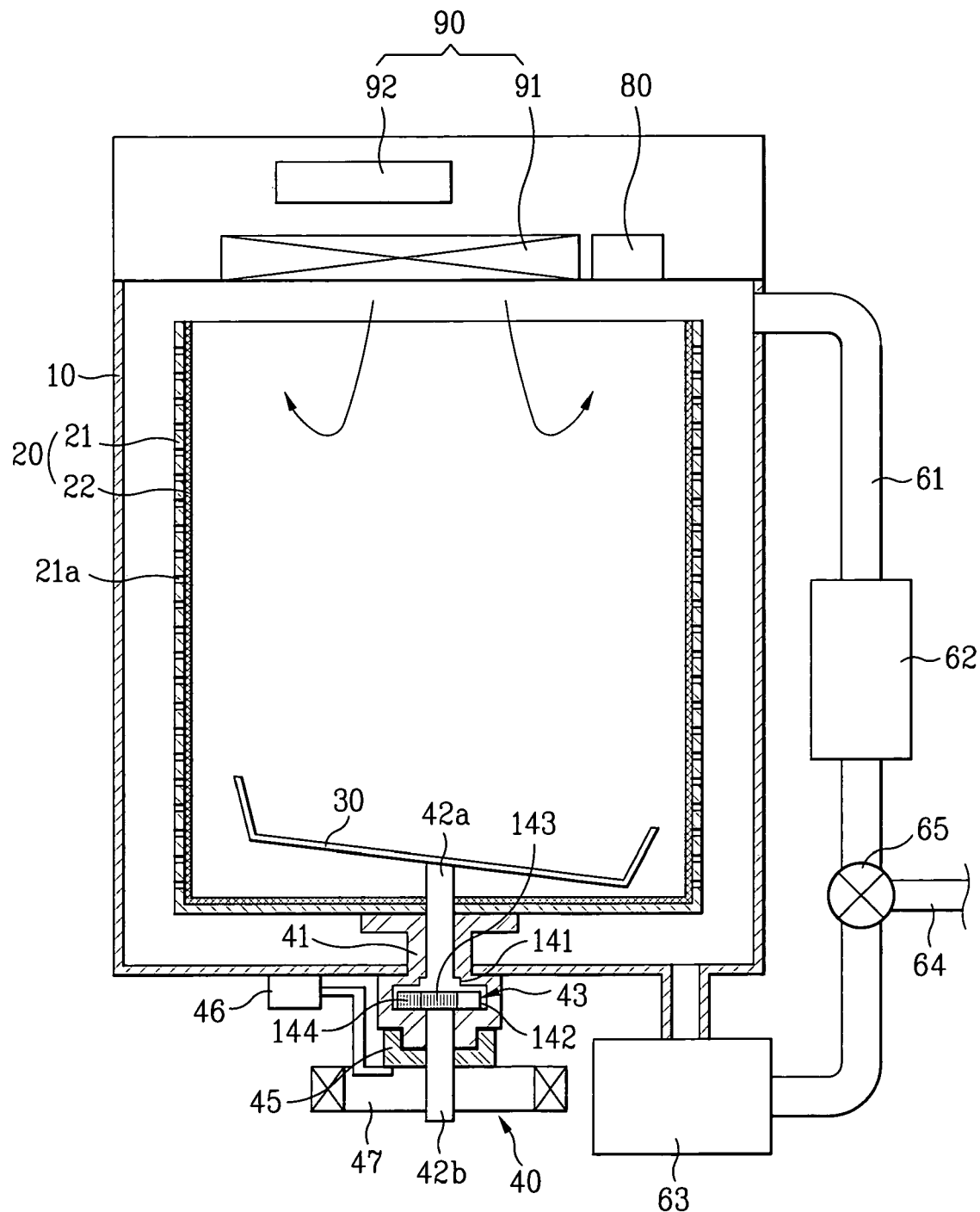
FIG. 5 illustrates a cross sectional view showing an organic matter disposer in accordance with a second embodiment of the present invention.

Meanwhile, FIG. 5 illustrates a structure of the organic matter disposer in accordance with a second embodiment of the present invention. As shown in FIG. 5, the organic matter disposer includes a tub 10, a drum 20, a fermentative microbe supplying unit 80, a stirrer 30, a driving device 40, and a heating device 90. IN this case, the tub 10, the stirrer 30, and the driving device 40 are the same as the first embodiment mentioned above, and thus description of which will be omitted. The circulating duct 61, the deodorizer 62, and the water tank 63 in accordance with the first embodiment of the present invention may also be applied to the second embodiment.

The fermentative microbe supplying unit 80 is provided at an upper part of the drum 20 so as to supply fermentative microbe to the organic matters. The fermentative microbe supplying unit 80 is opened and closed by a separate motor. The fermentative microbe supplying unit may also be formed in various forms so as to supply fermentative microbes to the drum 20.

The heating device 90 keeps the inside temperature of the drum 20 at a proper temperature so as to ferment organic matters. In this case, although the heating device 50 in accordance with the first embodiment needs a high temperature heater 51 so as to dry organic matters, the heating device 50 in the second embodiment needs a low temperature heater 91 for maintaining a relatively low temperature environment so as to ferment organic matters.

In this case, a fermenting speed of the organic matters is different according to an amount of moisture contained in the organic matters. Accordingly, a time needed for fermenting the organic matters is shortened by reducing amount of moisture contained in the organic matters and by separating moisture from the organic matters through the dehydrating step.

The heating device 90 includes a heater 91, and a fan 92. In this case, when the electric power is supplied, the heater 91 generates a predetermined temperature heat, and air heated by the heater is blown into the tub 10 by the fan 92.

Meanwhile, the drum 20 includes a body 21 having a plurality of through holes 21a formed thereon, and a screen 22 having a mesh formed in a size allowing to pass moisture through the plurality through holes 21a and to filter organic matters. In this case, the screen 22 is attached to an inner surface or an outer surface of the body 21. The structure of the drum 20 is the same as that of the firs embodiment mentioned above. The drum 20 of the second embodiment may include a bit low heat-proof material because the heater 91 generates relatively low temperature heat. Therefore, manufacturing cost of the drum 20 is reduced.

The organic matter disposer performs a dehydrating step and a fermenting step. In this case, the dehydrating step of the second embodiment is substantially the same as that of the first embodiment and thus description of which will be omitted.

The fermenting step will be described as follows. First, after completion of the dehydrating step, fermentative microbes are supplied into the drum by the fermentative microbe supplying unit 80. In this instance, only the stirrer axes 42a and 42b are rotated at a reduced speed. Accordingly, the stirrer 30 is rotated to stir organic matters in the drum 20. In this instance, the stirrer 30 is driven at a lower speed compared to the rotational speed of the drum 20 during the dehydrating step.

When the electric power is supplied to the heater 91, air is heated, and the heated air is supplied to organic matters by the fan 92. In this instance, the inside of the drum 20 is desirably maintained by the heated air at a temperature suitable for fermentation. The temperature suitable for fermentation is properly set according to a kind of microbe. Therefore, the organic matters are heated for a predetermined temperature so as to be stirred and fermented.

Figure 6:
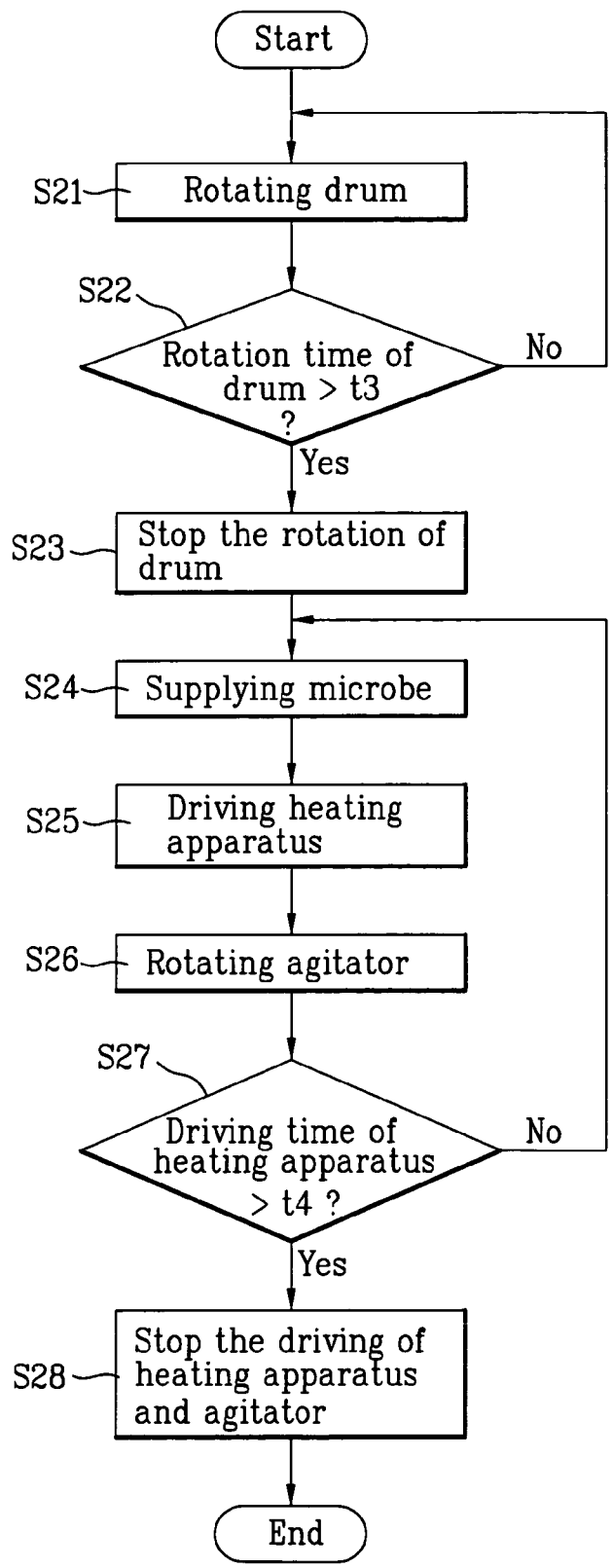
FIG. 6 illustrates a flow chart showing a method of controlling the organic matter disposer in accordance with the second embodiment of the present invention.

FIG. 6 illustrates a method of controlling the organic matter disposer in accordance with the second embodiment of the present invention. As shown in FIG. 6, when the dehydrating step is started, the drum is rotated (S21). The drum is rotated at a high speed so as to separate moisture from the organic matters, the moisture contained in the organic matters, and thereby to discharge the moisture to an outside thereof. In this instance, the drum is rotated at a high speed of about 20-50 rpm.

When the drum is rotated for a predetermined time that is set in the controlling member, the drum is stopped (S22 and S23). In this instance, the time for rotating the drum is preset in the controlling member according to amount of organic matters. The rotation time is of course may be set to be the same all the time.

When the dehydrating step is completed, the fermenting step is started. In this case, the fermenting step is started right after the dehydrating step is completed or after a predetermined time is passed. During the fermenting step, fermentative microbes are introduced from the fermentative microbe supplying unit into the drum (S24). In this instance, although the fermentative microbes may be supplied manually, the fermentative microbe supplying unit is desirably configured to supply the fermentative microbes automatically.

When the heating device is driven, relatively low temperature air that is heated by the heater is supplied to organic matters (S25). Accordingly, fermentative microbes are increased in the drum which is maintained at a proper temperature for fermentation. In this instance, the heater is desirably preheated a predetermined time before the drum is stopped because it takes some time for the heater to generate heat at a steady state temperature. In order for the heater to reach a desired temperature faster, the fan is also stopped when the heater is preheated.

Meanwhile, during the fermenting step, the stirrer is rotated at a low speed to stir organic matters (S26). Accordingly, contact area between the heated air and organic matters is increased. Therefore, a fermenting time is reduced and the organic matters are evenly fermented.

When the driving time of the heating device is reached a predetermined time (t14), the heating device and the stirrer are stopped (S27 and S28). In this case, the time for driving the heating device and the stirrer is desirably preset in the controlling member according to amount of organic matters.

As aforementioned, the organic disposer in accordance with the present invention has effects as follows. First, a drying time or a fermenting time is reduced and also electric power needed for the drying and fermenting steps is reduced because the organic matter disposer separates moisture from organic matters and then dries organic matters Second, since the heater preheats after the completion of the dehydrating step or before the fermenting step is started, the heater generates heat and reaches a normal operating temperature quickly and thus a time needed for a normal operation of the heater is reduced.

Third, moisture contained in the organic matters is separated through the dehydrating step, and thus amount of moisture contained in the organic matters is rapidly reduced. Therefore, a time needed for fermenting the organic matters is reduced.

Fourth, since the organic matters are stirred by the stirrer during the drying step or the fermenting step, the organic matters are more quickly and evenly dried.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An organic matter disposer comprising:
   a tub;
   a drum rotatably provided in the tub so as to store organic matters therein;
   a stirrer provided in the drum so as to stir the organic matters;
   a driving device for rotating the drum and the stirrer; and
   a heating device for drying the organic matters.

2. The organic matter disposer of claim 1, wherein the drum comprises a body having at least one through holes so as to discharge moisture contained in the organic matters.

3. The organic matter disposer of claim 2, wherein the drum further comprises a screen having a mesh for passing moisture through the through holes and filtering organic matters.

4. The organic matter disposer of claim 3, wherein the screen is attached to an inner or outer surface of the body.

5. The organic matter disposer of claim 1, further comprising a fermentative microbe supplying unit provided at an upper part of the drum so as to supply fermentative microbes to the organic matters.

6. The organic matter disposer of claim 1, wherein the driving device comprises:
   a dehydrating axis coupled with the drum;
   a stirrer axis rotatably provided in the dehydrating axis and coupled with the stirrer;
   a clutching device provided to selectively connect the dehydrating axis with the stirrer; and
   a motor for rotating the stirrer axis.

7. The organic matter disposer of claim 6, wherein the stirrer axis comprises:
   an upper stirrer axis connected with the stirrer; and
   a lower stirrer axis connected with the motor.

8. The organic matter disposer of claim 7, further comprising a speed reducer provided between the upper stirrer axis and the lower stirrer axis so as to reduce rotational speed transmitted from the motor.

9. The organic matter disposer of claim 8, wherein the speed reducer comprises:
   a sun gear provided at an upper end of the lower stirrer axis;
   a planetary gear connected with the sub gear;
   a first inner gear formed at a lower part of the upper stirrer axis so as to be selectively connected with the sun gear; and
   a second inner gear formed at a lower part of the first inner gear so as to be selectively connected with the sun gear.

10. The organic matter disposer of claim 6, wherein the clutching device comprises:
    a coupling provided to be movable up and down at an outer circumference of the lower stirrer axis so as to be selectively connected with the dehydrating axis; and
    a clutch for moving the coupling up and down.

11. The organic matter disposer of claim 1, wherein heating device comprises:
    a heater for heating air; and
    a fan for blowing air into the tub, the air heated by the heater.

12. A method of controlling an organic matter disposer, comprising:
    a dehydrating step of discharging moisture contained in organic matters by rotating a drum and a stirrer at a predetermined speed; and
    a drying step of rotating the stirrer and blowing air into the drum, the air heated by the heating device.

13. The method of claim 12, wherein in the drying step, the stirrer is rotated at a reduced speed.

14. The method of claim 12, wherein in the dehydrating step, the drum and the stirrer are rotated at a same speed.

15. The method of claim 12, further comprising, before the drying step, a preheating step of preheating the heating device.

16. The method of claim 15, wherein the preheating step is performed for a predetermined time preset in a controlling member and then automatically stopped.

17. The method of claim 12, wherein the dehydrating step is performed for a predetermined time preset in a controlling member and then automatically stopped.

18. The method of claim 12, wherein the drying step is performed for a predetermined time preset in a controlling member and then automatically stopped.

19. A method of controlling an organic matter disposer, comprising:
    a dehydrating step of discharging moisture contained in organic matters by rotating a drum and a stirrer at a predetermined speed;
    a supplying step of supplying fermentative microbes into the drum; and
    a fermenting step of fermenting the organic matters by rotating the stirrer and blowing air into the drum, the air heated by a heating device.

20. The method of claim 19, wherein the heating device keeps the inside of the drum at a proper temperature for fermentation.

21. The method of claim 19, wherein in the fermenting step, the stirrer is rotated at a reduced speed.

22. The method of claim 19, wherein in the dehydrating step, the drum and the stirrer are rotated at a same speed.

23. The method of claim 19, further comprising, before the drying step, a preheating step of preheating the heating device.

24. The method of claim 23, wherein the preheating step is performed for a predetermined time preset in a controlling member and then automatically stopped.

25. The method of claim 19, wherein the dehydrating step is performed for a predetermined time preset in a controlling member and then automatically stopped.

26. The method of claim 19, wherein the drying step is performed for a predetermined time preset in a controlling member and then automatically stopped.

* * * * *